US00PP26358P3

(12) United States Plant Patent
Egger

(10) Patent No.: US PP26,358 P3
(45) Date of Patent: Jan. 26, 2016

(54) *HEUCHERA* PLANT NAMED 'TNHEUFP'

(50) Latin Name: ***Heuchera* hybrid**
Varietal Denomination: TNHEUFP

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 150 days.

(21) Appl. No.: 13/999,448

(22) Filed: Feb. 25, 2014

(65) Prior Publication Data

US 2015/0245553 P1 Aug. 27, 2015

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by leaves which are colored deep purple colored year round, medium size, glossy leaves with fluted margins, purple pink flowers on dark peduncles, great winter foliage color, a medium, mounding habit, a high crown count, excellent tolerance to heat and humidity, and excellent vigor.

1 Drawing Sheet

Botanical denomination: *Heuchera* hybrid.
Variety designation: 'TNHEUFP'.

BACKGROUND OF THE INVENTION

The present invention relates to a new and distinct cultivar of *Heuchera* and given the cultivar name of 'TNHEUFP'. *Heuchera* is in the family Saxifragaceae. *Heuchera* 'TNHEUFP' originated as a controlled cross using *Heuchera* K608-2, a proprietary, unnamed plant as the seed parent, and *Heuchera* K698-6, a proprietary, unnamed plant as the pollen parent.

Compared to the seed parent K608-2, the new cultivar the new cultivar has leaves that have a stronger purple color and flowers that are on shorter inflorescences.

Compared to the pollen parent K698-6, the new cultivar has leaves that have a stronger purple color.

Compared to *Heuchera* 'Grape Soda', U.S. Plant patent application Ser. No. 13/999,447, the new cultivar has deep purple foliage rather than rose to light plum.

Compared to *Heuchera* 'Georgia Plum', U.S. Plant Pat. No. 24,507, the new cultivar has deep purple foliage rather than rose to light plum.

This new *Heuchera* is uniquely distinguished by:

1. leaves deep purple colored year round,
2. medium size, glossy leaves with fluted margins,
3. purple pink flowers on dark peduncles,
4. great winter foliage color,
5. a high crown count,
6. a medium, mounding habit,
7. excellent tolerance to heat and humidity,
8. and excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a close up of an eight-month-old plant of *Heuchera* 'TNHEUFP' in bloom growing in a one gallon container, grown in a warm greenhouse in July in Canby, Oreg.

FIG. 2 shows nine-month-old plants growing in the trial beds in September in Canby, Oreg.

DETAILED PLANT DESCRIPTION

The following is a detailed description of the new *Heuchera* cultivar based on observations taken in late June of one and one-half-year-old specimens growing in one gallon containers, grown outside in a shade house in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart*, $5^{th}$ edition.

Plant:

*Form.*—Basal rosette, herbaceous perennial.

*Hardiness.*—USDA Zone 4 to 9.

*Size.*—18 cm tall from top of the foliage to the ground and 44 cm wide (two-year-old plants grow to 55 cm wide and 30 cm tall).

*Number of crowns.*—9.

*Habit.*—Mounding.

*Vigor.*—Excellent.

Leaf:

*Type*.—Simple.

*Arrangement*.—Rosette.

*Shape*.—Broadly ovate.

*Lobing/division*.—5 to 7 shallow lobes, the terminal the longest, shallow secondary lobes.

*Venation*.—Palmate.

*Margins*.—Crenate, fluted.

*Apex*.—Mucronulate.

*Base*.—Cordate.

*Blade size*.—Grows to 11 cm long and 10.5 cm wide.

*Surface texture*.—Glandular on both sides.

*Rugosity*.—Absent.

*Petiole description*.—Grows to 17 cm long and 2.5 mm wide, glandular hairs, Purple N79B.

*Leaf color*.—Topside, leaves all year closest to Purple N79A with veins Black 203C, bottom side Purple N79A with veins N79B.

Inflorescence:

*Size*.—Grows to 3.5 cm wide and 9 cm long, often bending over.

*Type*.—Thyrse.

*Number of flowers per thyrse*.—About 40.

*Number of thyrse*.—About 6.

*Peduncle*.—Grows to 21 cm long and 4 mm wide at base, Red Purple 59A on bottom blending to Violet Blue N92A on top, glandular hairs.

*Pedicel*.—Variable in size, with glandular hairs, closest to Violet Blue N92A.

*Attitude*.—Upwards to semi-upwards.

*Bloom period*.—Sporadic bloom spring through summer.

Flower bud:

*Size*.—3 mm wide and 4 mm long.

*Description*.—Glandular puberulent, ovoid, down facing.

*Color*.—Red Purple 71C on bottom half to 71D on top half.

Flower:

*Type*.—Perfect.

*Shape*.—Campanulate.

*Attitude*.—Outward to semi-downwards.

*Size*.—8 mm long and 5.5 mm wide.

*Corolla description*.—5 petals, 3 mm long and less than 1 mm wide, linear, margins entire, tip acute, glabrous on top and glandular on bottom side, Purple 75C on both sides.

*Calyx description*.—Campanulate, 8 mm long and 5.5 mm wide, with 5 lobes divided ½ way to the base, each 2 mm wide and 3 mm long, glandular on top and bottom, tip obtuse, margin entire; color inside Purple 75C, outside Red Purple 71C on bottom half to Purple 75C with lobe centers Red Purple 71C on top half.

*Stamen description*.—5 in number, filaments 2 mm long, Purple 75D, anthers 0.4 mm, Greyed Orange 177B, no pollen.

*Pistil description*.—1, 2-beaked, 6 mm long and 1.8 mm wide, ovary 2 mm long and 1.8 mm wide, Red Purple 64C, style 4 mm long, Purple 75C.

*Fragrance*.—None.

*Lastingness*.—Each thyrse blooms for about 3 weeks on the plant.

Fruit:

*Type*.—Two-beaked ovoid capsule.

*Fertility*.—Low.

*Color*.—Greyed Brown 199C.

Seed:

*Shape*.—Linear.

*Size*.—1 mm long.

*Color*.—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

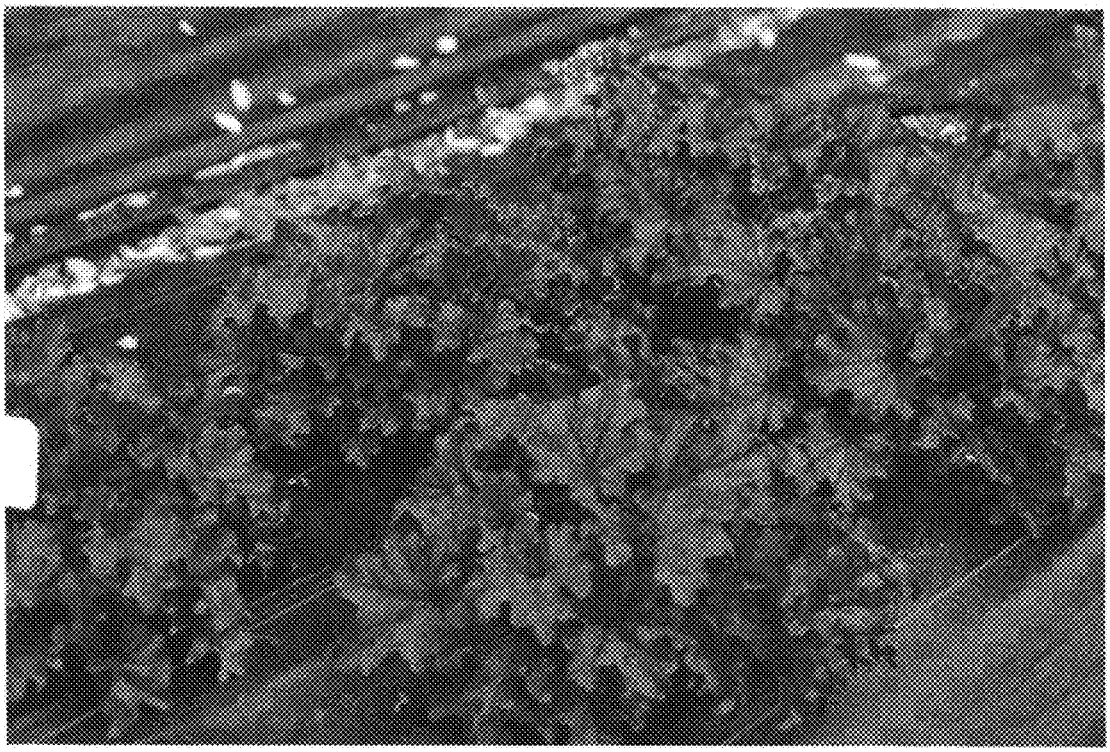

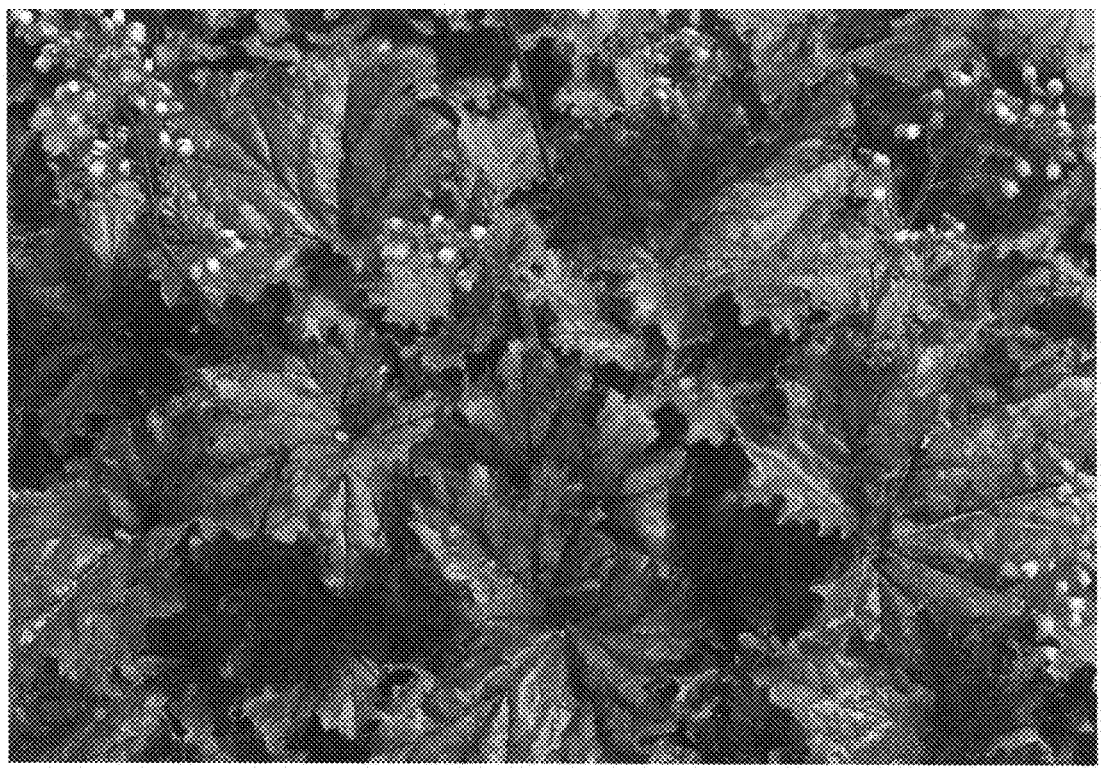
FIG. 1 above, FIG. 2 below